United States Patent
Pappas et al.

(10) Patent No.: US 8,382,817 B2
(45) Date of Patent: *Feb. 26, 2013

(54) ENDOPROSTHESES FOR PERIPHERAL ARTERIES AND OTHER BODY VESSELS

(75) Inventors: Jeffrey Pappas, Santa Clara, CA (US); Sanjay Shrivastava, Mountain View, CA (US)

(73) Assignee: Abbott Laboratories, Abbott Park, IL (US)

( * ) Notice: Subject to any disclaimer, the term of this patent is extended or adjusted under 35 U.S.C. 154(b) by 130 days.

This patent is subject to a terminal disclaimer.

(21) Appl. No.: 12/911,324

(22) Filed: Oct. 25, 2010

(65) Prior Publication Data

US 2011/0040370 A1    Feb. 17, 2011

Related U.S. Application Data

(62) Division of application No. 11/769,410, filed on Jun. 27, 2007, now Pat. No. 7,867,273.

(51) Int. Cl.
*A61F 2/82* (2006.01)
(52) U.S. Cl. .................................................... 623/1.15
(58) Field of Classification Search ......... 623/1.11–1.36
See application file for complete search history.

(56) References Cited

U.S. PATENT DOCUMENTS

| | | | |
|---|---|---|---|
| 5,807,404 A | 9/1998 | Richter | |
| 5,810,872 A | 9/1998 | Kanesaka et al. | |
| 5,827,321 A | 10/1998 | Roubin et al. | |
| 5,843,175 A | 12/1998 | Frantzen | |
| 5,876,449 A | 3/1999 | Starck et al. | |
| 5,913,895 A | 6/1999 | Burpee et al. | |
| 5,931,866 A | 8/1999 | Frantzen | |
| 5,938,682 A | 8/1999 | Hojeibane et al. | |
| 6,042,597 A | 3/2000 | Kveen et al. | |
| 6,083,259 A | 7/2000 | Frantzen | |
| 6,117,165 A | 9/2000 | Becker | |
| 6,261,319 B1 * | 7/2001 | Kveen et al. | 623/1.15 |
| 6,325,821 B1 | 12/2001 | Gaschino et al. | |
| 6,451,049 B2 | 9/2002 | Valiana et al. | |
| 7,056,550 B2 | 6/2006 | Davila et al. | |
| 7,162,303 B2 | 1/2007 | Levin et al. | |
| 7,491,228 B2 * | 2/2009 | Doran et al. | 623/1.15 |
| 7,867,273 B2 * | 1/2011 | Pappas et al. | 623/1.15 |
| 2007/0060921 A1 | 3/2007 | Janssen et al. | |

FOREIGN PATENT DOCUMENTS

EP      1197189      4/2002

* cited by examiner

*Primary Examiner* — Suzette J Gherbi
(74) *Attorney, Agent, or Firm* — Jonathan D. Feuchtwang; Fulwider Patton LLP

(57) ABSTRACT

An endoprostheses for implanting in a body lumen, such as a coronary artery, peripheral artery, or other body lumen includes a plurality of elongate strut members spaced apart and extending along a longitudinal axis, each elongate strut member having a plurality of alternating peaks and valley. At least one flexible connecting link connects each elongate strut member to an adjacent elongate strut member. The elongate strut members and connecting links forming a generally tubular stent body having a first delivery diameter and a second implanted diameter. The positioning of the connecting links along the stent body produces desired stent performance characteristics.

6 Claims, 8 Drawing Sheets

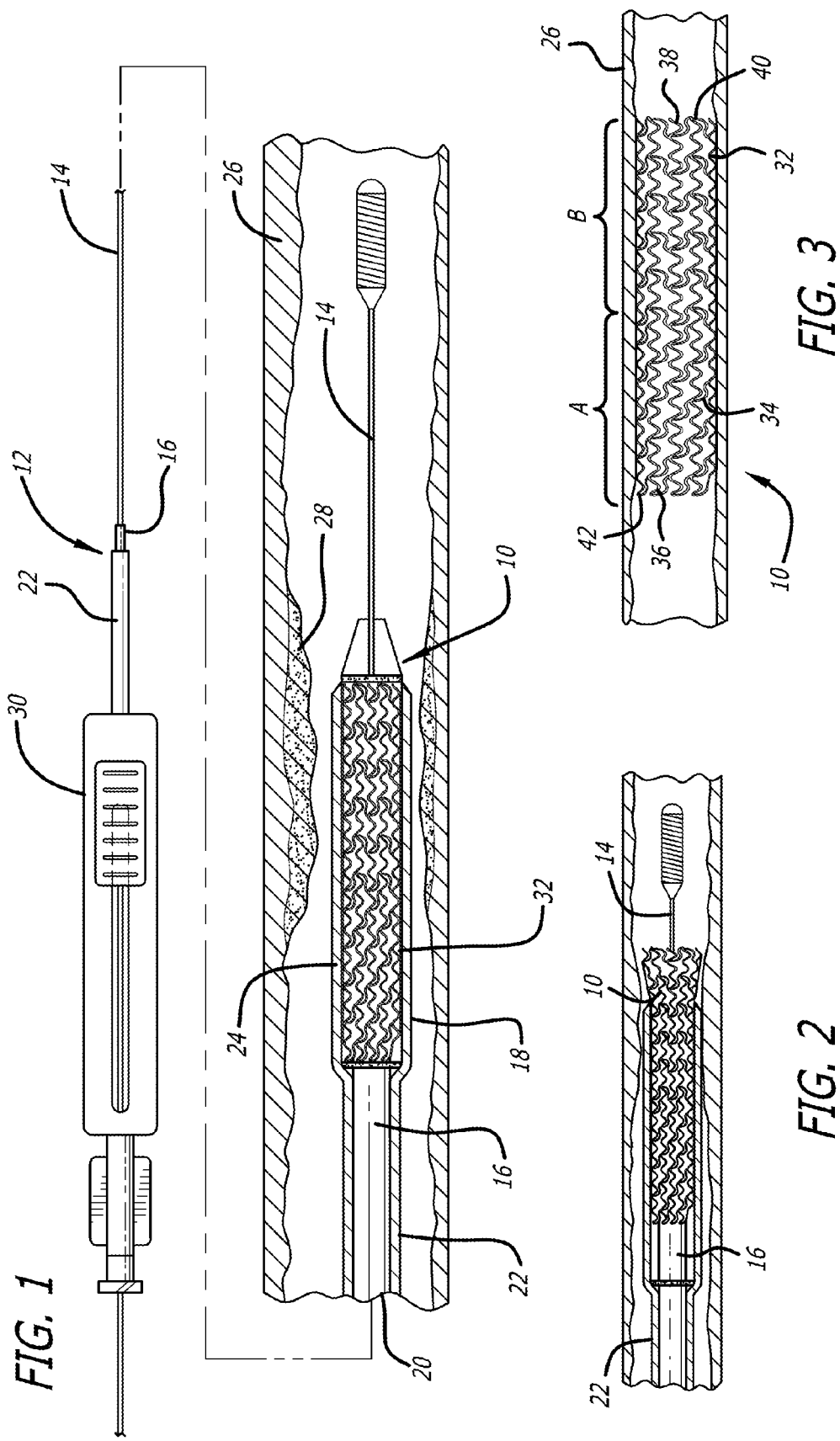

ENDOPROSTHESES FOR PERIPHERAL ARTERIES AND OTHER BODY VESSELS

CROSS-REFERENCE TO RELATED APPLICATIONS

This application is a divisional of U.S. Ser. No. 11/769,410, filed on Jun. 27, 2007, which issued as U.S. Pat. No. 7,867,273.

BACKGROUND OF THE INVENTION

The invention relates generally to vascular repair devices, and in particular to endoprostheses, more commonly referred to as intravascular stents, which are adapted to be implanted into a patient's body lumen, such as a blood vessel or artery, to maintain the patency thereof. Stents are particularly useful in the treatment of atherosclerotic stenosis in arteries and blood vessels. More particularly, the present invention is directed to an intravascular stent that has a pattern or configuration that permits the stent to be placed in body vessels which are susceptible to physiological deformations and provides a high degree of fracture and fatigue resistance to such deformations.

Peripheral Artery Disease, or PAD, is characterized by fatty plaque build-up in the arteries of the legs, which results in poor blood flow and circulation. Patients with PAD may experience muscle pain during walking, have wounds and ulcers that are slow to heal or, in the most severe cases, require amputation of the legs. Possible treatments for PAD include lifestyle modification (including cessation of smoking), medicines, balloon dilatation, metal stent placement or bypass surgery.

Stents are generally tubular-shaped devices which function to hold open a segment of a blood vessel or other body lumen such as a coronary or peripheral artery. They also are suitable for use to support and hold back a dissected arterial lining that can occlude the fluid passageway. At present, there are numerous commercial stents being marketed throughout the world. While some of these stents are flexible and have the appropriate radial rigidity needed to hold open a vessel or artery, there typically is a tradeoff between flexibility and radial strength.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from shape memory metals or superelastic nickel-titanium (NiTi) alloys, which will automatically expand from a compressed state when the stent is advanced out of the distal end of the delivery catheter into the blood vessel. Such stents manufactured from expandable heat sensitive materials usually allow for phase transformations of the material to occur, resulting in the expansion and contraction of the stent.

Stents can be implanted in the coronary arteries along with peripheral arteries, such as the renal arteries, the carotid arteries and in long arterial segments in the leg, all of which are susceptible to arteriosclerosis. Generally, balloon-expandable stents have been implanted in the coronary arteries since the coronary arteries are generally not vulnerable to bending and compression forces that can distort the stent structure. Typically, balloon-expandable stents are made from a stainless steel or cobalt-chromium alloy, multi-layer materials or other similar biocompatible materials. Peripheral vessels, on the other hand, are usually more prone to natural bending and compressive forces which can easily bend and distort the implanted stent, causing it to fracture. For this reason, self-expanding stents are usually implanted in peripheral vessels since the self-expanding properties of the stent allows it to spring back to shape even after being subjected to bending or compressive forces.

Peripheral stents can be much longer than coronary stents since longer segments of the peripheral artery are usually required to be treated. The current trend for manufacturing peripheral stents is moving towards a longer stent, typically about 80-120 mm and longer, to treat long arterial segments in patients with critical limb ischaemia (CLI) in such arteries as, for example, the superficial femoral artery (SFA), along with arteries below the knee. Long segments of the peripheral arteries, such as the ilio-femoral-popliteal artery, usually have regions where bending and compressive forces are so constant and repetitive that even a self-expanding stent can be subjected to possible deformation caused by fatigue and fracturing. Other regions of peripheral arteries are subject to compressive forces which can prevent the stent from possibly spring back to its open, expanded configuration which can lead to stent fracture as well. For example, it has been shown that the ilio-femoral-popliteal segment undergoes non-pulsatile deformations which will, in turn, act on any stent implanted in this arterial segment. These deformations have been identified as being axial, torsional and/or bending and specific segments of the superficial femoral artery have been associated with specific non-pulsatile deformations. These deformations can impinge on the stent's ability to maintain these arteries in a fully opened position and can result in deformation and fracturing of the often intricate strut patterns. Moreover, while one stent pattern may be suitable for a particular segment of artery, the same stent pattern may not be suitable for implantation in an adjacent arterial segment if a different type of non-pulsatile deformation is present in the adjacent arterial segment.

In many procedures which utilize stents to maintain the patency of the patient's body lumen, the size of the body lumen can be quite small which prevents the use of some commercial stents which have profiles which are entirely too large to reach the small vessel. Many of these distal lesions are located deep within the tortuous vasculature of the patient which requires the stent to not only have a small profile, but also high flexibility to be advanced into these regions. As a result, the stent must be sufficiently flexible along its longitudinal axis, yet be configured to expand radially to provide sufficient strength and stability to maintain the patency of the body lumen. Moreover, the stent and its delivery system must possess sufficient axial strength to achieve the needed pushability to maneuver the stent into the area of treatment.

What has been needed and heretofore unavailable is a stent which has a high degree of flexibility so that it can be advanced through tortuous passageways and can be radially expanded in a body segment which is susceptible to physiological deformations, and yet possesses sufficient mechanical strength to hold open the body lumen or artery to provide adequate vessel wall coverage while attaining a high degree of fracture and fatigue resistance. Such a stent should be able to match the physiological deformations associated in various regions of the body vessel to effectively provide a high level of fracture and fatigue resistance to the various loading conditions and deformation patterns to which the stent may be subjected. The present invention satisfies these and other needs.

SUMMARY OF THE INVENTION

The present invention is directed to an intravascular stent that has a strut pattern or configuration that permits the stent to be placed in body vessels which are susceptible to certain physiological deformations and provides a high degree of fracture and fatigue resistance to the particular deformation. The stent is highly flexible along its longitudinal axis to facilitate delivery through tortuous body lumens, but is stiff and stable enough radially in its expanded condition to maintain the patency of a body lumen, such as an artery, when the stent is implanted therein.

A composite stent made in accordance with the present invention can be formed with multiple stent segments, each stent segment have a different stent performance characteristic designed to match the physiological deformation present in the vessel segment in which that particular stent segment will be implanted. Accordingly, specific strut patterns can be created on specific stent segments to provide a high degree of fracture and fatigue resistance to a particular physiological deformation. For example, stent segments with strut patterns which provide particularly high levels of fracture and fatigue resistance to torsional loading, bending loading or axial loading can be created and disposed along the length of the composite stent to match the type of loading to which the stent segment will be subjected. An axially or torsionally more flexible stent is likely to have lower stress when subjected to some deformation thereby producing enhanced resistance to deformation fracture or fatigue. A single composite stent having different performance characteristics can be created and implanted in long vessel segments, such as the ilio-femoral-popliteal arterial segment, to match the different physiological deformations encountered in each region of the arterial segment. Alternatively, in accordance with the present invention, a single stent segment could be manufactured into a single stent and implanted in a body vessel to provide the desired stent performance need for that particular body vessel.

The present invention generally includes a plurality of elongate strut members that are spaced apart and extend along a longitudinal stent axis. These elongate strut members are interconnected to form a portion of the body of the stent. In one embodiment, connecting links are integrally formed to connect adjacent elongate strut members together to cooperatively form the tubular stent body. These connecting links are designed to cause the elongate strut members to expand radially outward from a collapsed position to a radially expanded position. Not only do these connecting links provide flexibility and expandability to the stent body, but the positioning of the connecting links achieves different stent performance characteristics needed for a particular application. As addressed above, the particular stent pattern can be used individually to create a single stent or different stent segments having different performance characteristics can be combined to create a long, composite stent.

Each of the elongate strut members rings making up the stent has a proximal end and a distal end. The distal ends of the elongate strut members are connected together to form the distal end of the stent. Likewise, the proximal ends of the elongate strut members are connected together to create the proximal end of the stent. In one aspect of the invention, each elongate strut member has a serpentine or undulating shape. The shape can be, for example, alternating peaks and valley which forms a sinusoidal wave. Generally, the undulating pattern of the elongate strut member can include U-shaped or V-shaped elements, although other shapes could be used as well.

Each elongate strut member is connected to an adjacent elongate strut member by at least one connecting link. These connecting links are highly flexible and allow the stent to attain highly flexible along its longitudinal axis. The connecting links are disposed along the length of the stent in selective patterns which achieve and promote high levels of fracture and fatigue resistance for particular loading associated with different segments of a patient's vasculature. In one embodiment, the connecting links are placed along the circumference of the stent body and align end to end in a "helix" pattern that winds around the stent body. This particular pattern of connecting links provide high fracture and fatigue resistance when the stent is subjected to torsional loading when implanted in the patient's vasculature. This particular pattern of connecting links results in a large expanded radius which results in stress being distributed over a greater area, resulting in less fatigue and less potential for stent fracture resulting from repetitive motion. This stent pattern provides excellent longitudinal flexibility while still providing good torsional flexibility once implanted in the patient.

In another aspect of the present invention, another strut pattern can be created by utilizing a set of connecting links placed along the body of the stent in a "stacked" configuration so that the connecting links are located laterally adjacent to each other in a plane that is substantially perpendicular to the stent longitudinal axis. In this particular configuration, each connecting link is disposed laterally adjacent to another to form a circumferential "ring-like" pattern which extends about the circumference of the stent body. This particular pattern of connecting links provides high fracture and fatigue resistance particularly when the stent is subjected to bending loading when implanted in the patient's vasculature. This particular pattern of connecting links also results in a concentration of stacked connecting links which increases the radial strength of the stent body and provides good flexibility.

This stacked connecting link pattern described above can be varied to create yet another embodiment of a stent segment which achieves different stent performance characteristics. In this aspect of the invention, connecting links are placed along the body of the stent in an "offset-stacked" configuration, i.e., connecting links are placed on alternating elongated strut members and are aligned laterally adjacent to each other. In this configuration, there is an "offset" of connecting links which results in every other connecting link in the set remaining laterally aligned with another in a plane that is substantially perpendicular to the stent longitudinal axis. This particular pattern of connecting links provides high fracture and fatigue resistance particularly when the stent is subjected to axial loading when implanted in the patient's vasculature. This particular pattern of connecting links results in a stent segment having radial strength and flexibility evenly distributed throughout the length of the stent.

In another aspect of the present invention, as addressed above, two or more stent segments having different stent performance characteristics (i.e. different connecting link patterns) can be combined to create a composite stent. Each stent segment can be formed with the particular pattern of connecting links described above, namely the helix pattern, the stacked pattern and offset-stacked pattern. For example, in one particular embodiment, a stent segment made with multiple sets of stacked connecting links could be combined with a stent segment having connecting links disposed in the pattern which forms the continuous helix. This allows the stent manufacturer to create a stent having the desired stent characteristics which will match the physiological deformation conditions in regions of the body vessel in which each stent segment will be implanted. It should be appreciated that numerous combinations of stent segments can be attained to create various composite stents having different stent performance characteristics associated with the different segments forming the stent.

In another aspect of the present invention, the elongate strut members are formed of a plurality of peaks and valley where the peaks of the elongate strut members are aligned with each other. Likewise, the valley portions of the elongate strut members align with each other. The term "in phase" is commonly used to describe this alignment of peaks and valleys between adjacent elongated strut members. In this configuration, at least one connecting link attaches each elongate strut member to an adjacent strut member so that at least a portion of the connecting link is positioned within one of the peaks and it attaches the peaks to an adjacent peak.

While the elongate strut members and the connecting links generally are not separate structures, they have been conveniently referred to as elongate strut members and links for ease of identification. The number and location of connecting links can be varied as the application requires. In one embodiment, the connecting links have a bend or curved portion that will expand when the restraint placed on the self-expanding stent body is removed to allow the stent body to expand radially outwardly. When the connecting links expand, the overall longitudinal length of the stent generally remains virtually unchanged. The fact that the elongate strut members do not expand or contract when the stent is radially expanded maintains the overall length of the stent substantially the same whether in the unexpanded and expanded configurations. In other words, the stent should not substantially shorten upon expansion.

The stent may be formed from a tube by laser cutting the pattern of elongate struts and links in the tube. The stent also may be formed by laser cutting a flat metal sheet in the pattern of the elongate struts and links, and then rolling the pattern into the shape of the tubular stent and providing a longitudinal weld to form the stent. As used throughout the present application, the term adjacent may be used to define directly adjacent or indirectly adjacent.

Other features and advantages of the present invention will become more apparent from the following detailed description of the invention when taken in conjunction with the accompanying exemplary drawings.

BRIEF DESCRIPTION OF THE DRAWINGS

FIG. 1 is an elevational view, partially in section, of one particular embodiment of a stent made in accordance with the present invention mounted on a stent delivery catheter and positioned within an artery.

FIG. 2 is an elevational view, partially in section, similar to that shown in FIG. 1 wherein the stent is partially expanded within the artery, so that the stent contacts the arterial wall.

FIG. 3 is an elevational view, partially in section, showing the expanded stent implanted within the artery after withdrawal of the stent delivery catheter.

DETAILED DESCRIPTION OF THE PREFERRED EMBODIMENTS

Figure 4:
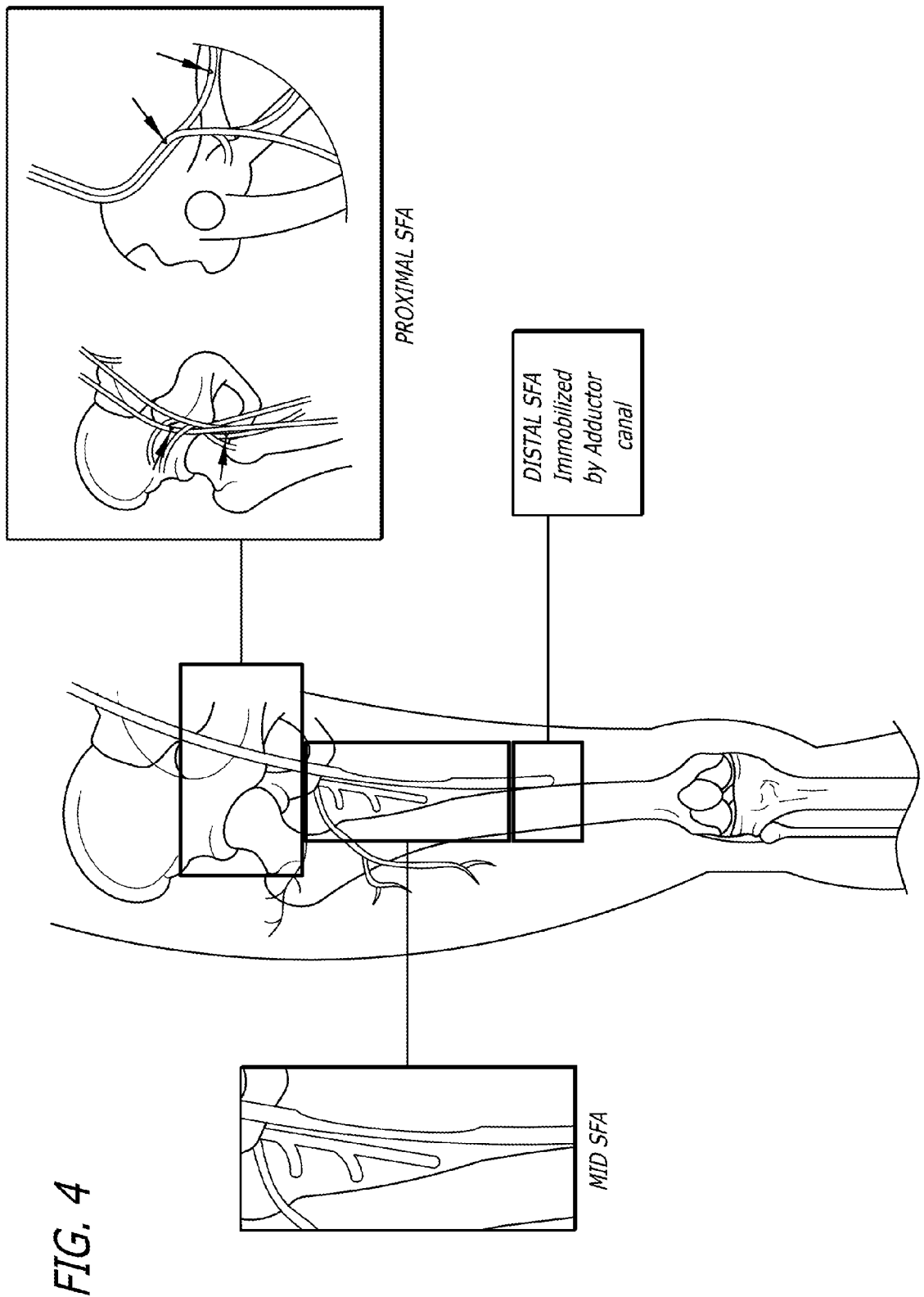
FIG. 4 is a schematic diagram which depicts an anterior view of the upper portion of the leg and the arterial structure found in this portion of the leg and the physio-mechanical environment in this arterial structure.

The present invention stent improves on existing stents by providing a longitudinally flexible stent having a uniquely designed pattern which has a high degree of fracture and fatigue resistance when subjected to physiological deformations associated with some body vessels. In addition to providing longitudinal flexibility, the stent of the present invention also provides radial rigidity and a high degree of scaffolding of a vessel wall, such as a peripheral artery.

Turning to the drawings, FIGS. 1-3 depicts a stent 10 made in accordance with the present invention mounted on a conventional catheter assembly 12 used to deliver the stent 10 and implant it in a body lumen, such as a peripheral artery, a coronary artery or other vessel within the body. The catheter assembly 12 is configured to advance through the patient's vascular system by advancing the catheter assembly 12 over a guide wire 14 using well known methods associated with over-the-wire or rapid-exchange catheter systems.

The catheter assembly 12, as depicted in FIGS. 1 and 2, is a typical self-expanding catheter delivery system which includes an inner member 16 having a stent mounting region 18 upon which the stent 10 is mounted. The inner member 16 includes a guide wire lumen 20 which receives the guide wire 14 and allows at least the distal portion of the catheter assembly 12 to slide over the guide wire 14. As is known in the art, the guide wire lumen 20 is sized for receiving various diameter guide wires to suit a particular application. The stent 10 is mounted on the stent mounting region 18 of the inner member 16 and is maintained in a delivery position by an outer member 22 having a retraining sheath 24 which extends over the stent 10 to maintain it in a collapsed position so that the stent 10 and catheter 12 present a low profile diameter for delivery through the peripheral arteries (or other vessels).

As shown in FIG. 1, a partial cross-section of an artery 26 is shown with a small amount of plaque 28 that has been previously treated by an angioplasty or other repair procedure. Stent 10 is used to repair a diseased or damaged arterial wall which may include plaque 28 as shown in FIGS. 1-3, or a dissection, or a flap of the arterial wall which is sometimes found in the peripheral and coronary arteries and other vessels.

In a typical procedure to implant the self-expanding stent 10, the guide wire 14 is first advanced through the patient's vascular system by using well known methods so that the distal end of the guide wire 14 is advanced past the plaque or diseased area 28. Prior to implanting the stent 10, the cardiologist may wish to perform an angioplasty procedure or other procedure (i.e., atherectomy) in order to open the vessel and remodel the diseased area. Thereafter, the stent delivery catheter assembly 12 is advanced over the guide wire 14 so that the stent 10 is positioned in the target area. The restraining sheath 24 of the outer member 22 can then be retracted using a proximal handle 30 (located outside of the patient) so that the stent 10 will gradually be uncovered, as depicted in FIG. 2, to allow it to expand radially outward until the stent 10 is fully apposed to the vessel wall as depicted on FIG. 3. The catheter 12 can then be withdrawn from the patient's vascular system. The guide wire 14 is typically left in the artery for possible post-dilatation procedures, if any, and subsequently is withdrawn from the patient's vascular system as well. A balloon catheter (not shown) can be used, if needed, to post-dilate the self-expanding stent 10. If the stent 10 is of the balloon-expandable variety, it can be delivered to the area of treatment using well known methods as well.

The stent 10 serves to hold open the artery 26 after the catheter is withdrawn, as illustrated by FIG. 3. Due to the formation of the stent 10 in the shape of an elongate tubular member, the undulating components of the stent 10 are relatively flat in transverse cross-section, so that when the stent is expanded, it is pressed into the wall of the artery and as a result does not interfere with the blood flow through the artery. The stent 10 is pressed into the wall of the artery and may eventually be covered with endothelial cell growth which further minimizes blood flow interference. The undulating portion of the stent provides good tacking characteristics to prevent stent movement within the artery. Furthermore, the closely spaced connecting links found at regular intervals along the length of the stent provide uniform support for the wall of the artery, as illustrated in FIG. 3.

Figure 5:
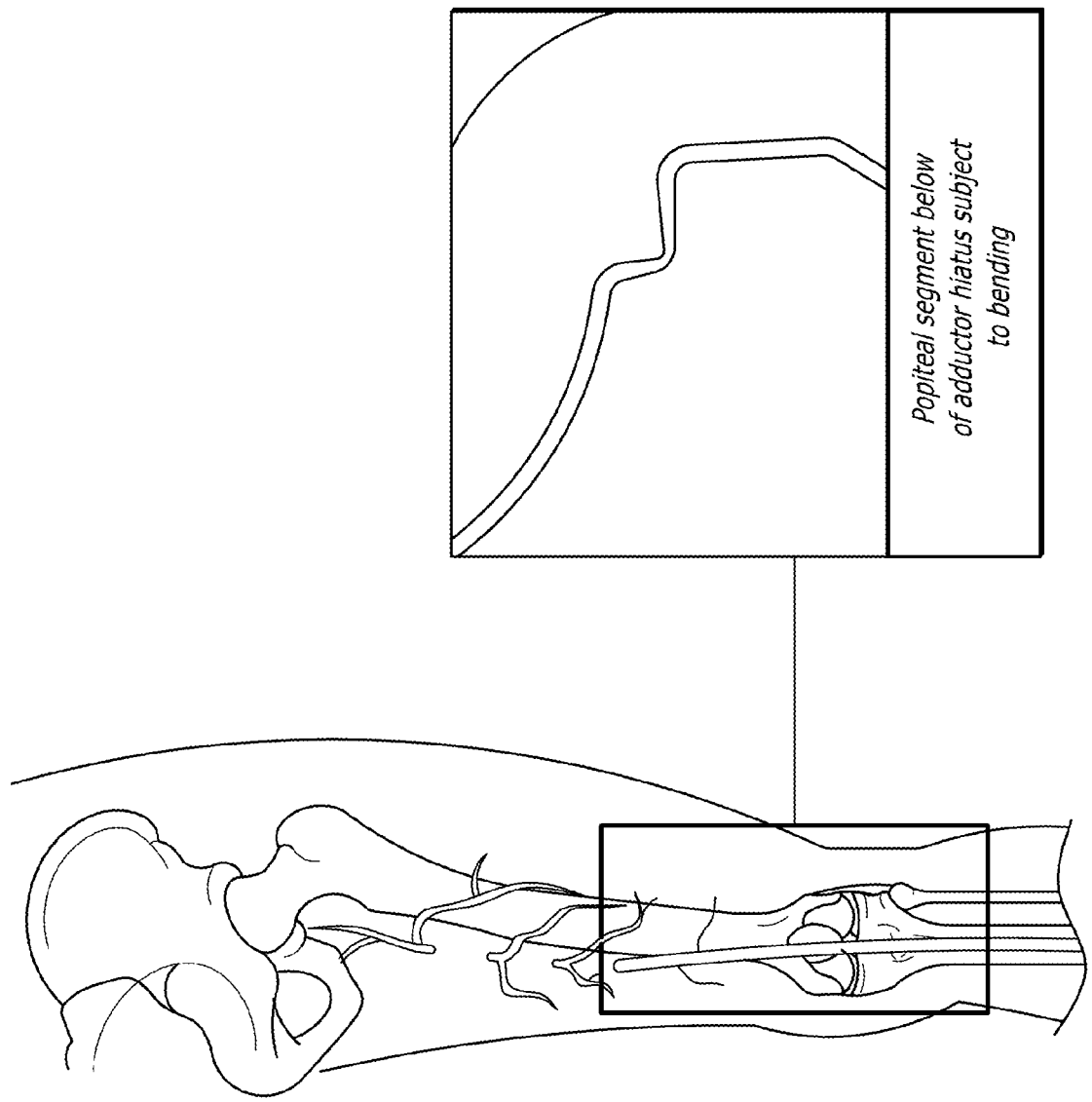
FIG. 5 is a schematic diagram which depicts a posterior view of the upper portion of the leg and the arterial structure found in this portion of the leg and the physio-mechanical environment in this arterial structure.

Referring now to FIGS. 4-5, schematic diagrams depict the anterior and posterior view of the upper portion of a human leg and the arterial structure found in this portion of the leg. This particular arterial segment is a prime site for implanting a stent made in accordance with the present invention. It has been demonstrated that ilio-femoral-popliteal arterial segment undergo non-pulsatile deformations. These deformations have further been identified to be axial, torsional and/or bending. Furthermore, specific segments of the superficial femoral artery can be associated with specific non-pulsatile deformation. FIG. 4 shows the anterior view of the upper leg and the arterial structure which includes the femoral artery, the proximal superficial femoral artery, the mid proximal superficial femoral artery and the distal superficial femoral artery. As can be seen in the diagrams, the proximal superficial femoral artery, sometimes referred to as the ilio-femoral segment, is subject to bending caused by movement of the leg. As a result, the proximal superficial femoral artery is subject to kinking at particular spots (identified by arrows in the top box) when the leg undergoes extension or flexion. This particular segment of the ilio-femoral-popliteal anatomy will be subject to continuous bending and kinking as the patient walks or runs. Accordingly, any stent implanted in this particular segment of the anatomy may be subject to the same kinking and bending experienced by this particular arterial segment.

The mid proximal superficial femoral artery is subject to a different type of physiological deformation, namely, torsional loading, which can cause this arterial segment to become compressed. The distal superficial femoral artery, shown near the knee joint, can be easily immobilized by the adductor canal which can cause unwanted axial loading on any stent implanted in this arterial segment.

Referring now to FIG. 5, the posterior view of the leg shows the femoral-popliteal segment below the adductor hiatus subject to bending or kinking as the leg moves. Kinking and bending of this arterial segment occurs, for example, when the leg undergoes 70% flexion. Any kinking or bending of the femoral-popliteal segment will likewise cause bending or kinking of any stent implanted in this particular arterial segment.

Figure 6:
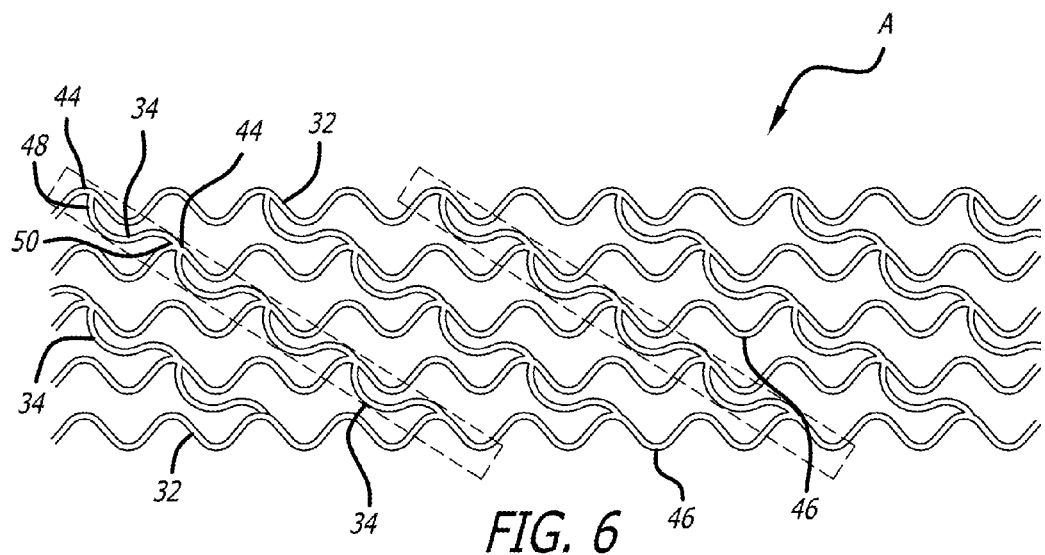
FIG. 6 is a plan view of a portion of the stent depicted in FIGS. 1-3.
Figure 7:
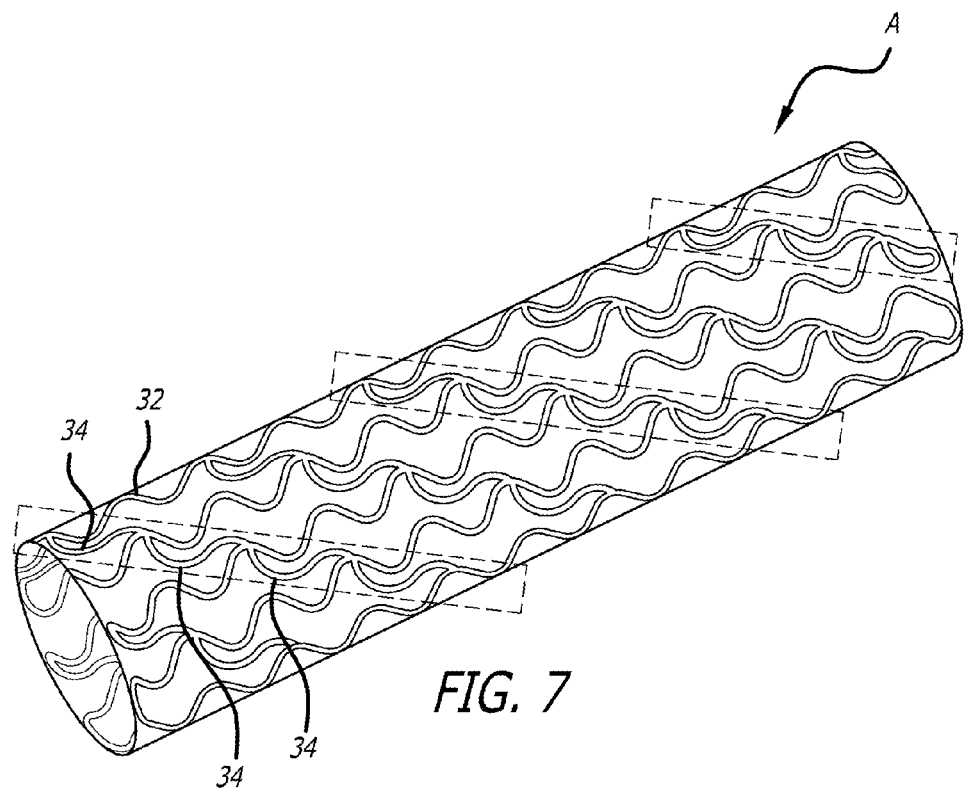
FIG. 7 is a perspective view of the stent of FIG. 6 in a fully expanded configuration.

In keeping with the present invention, FIGS. 6-15 depict the stent in various embodiments. FIGS. 6 and 8-13 show the stent in a flattened condition so that the pattern can be clearly viewed, even though the stent is in a cylindrical form in use, such as shown in FIG. 7. The stent is typically formed from a tubular member, however, it can be formed from a flat sheet and rolled into a cylindrical configuration.

Referring again to FIGS. 1-3, the particular strut patterns used to create the stent 10 are shown in the form of two stent segments A and B which combine together to create the long, composite stent 10. Each stent segment A and B has different stent performance characteristics than the other to allow the particular stent segment to be implanted in a particular portion of an arterial segment. The composite stent 10 can be fabricated using two or more stent segments having different stent performance characteristics to match the physiological deformations associated with the arterial segments in which the particular stent segments will be implanted. As a result, a composite stent having different regions of stent performance can be manufactured. Each individual stent segment can be made with a particular strut pattern which will provide high fracture and fatigue resistance under the loading condition and deformation patterns associated with the arterial segment in which the stent segment is implanted.

Figure 8:
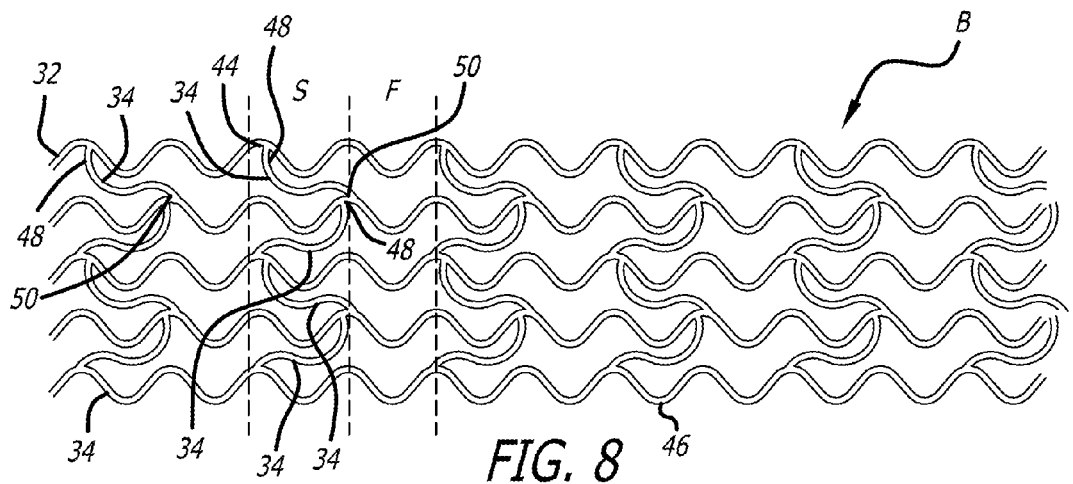
FIG. 8 is a plan view of a portion of the stent depicted in FIGS. 1-3.

Referring now to FIGS. 6-8, the particular stent patterns which forms the stent segments A and B are shown in greater detail. As can be seen from FIGS. 1-3 and 6-8, the stent 10 includes a number of elongate strut members 32 which are spaced apart and extend along lengthwise to define a longitudinal stent axis. These elongated strut members 32 are interconnected with each other utilizing connecting links 34 which cooperatively form the tubular stent body. These connecting links 34 are designed to cause the elongate strut members 32 to expand radially outward from a collapsed position having a delivery diameter to a radially expanded position having an expanded diameter. These connecting links 34 provide flexibility and expandability to the stent body, and the positioning of the connecting links 34 relative to each other achieves different stent performance characteristics. As will be explained below, the particular positioning of the connecting links 34 along the stent body achieves fatigue and fracture resistance in a response to the different physiological deformations associated with different arterial segment of the patient's vasculature.

As can be seen in FIGS. 1-6, each elongated strut member 32 has a proximal end 36 and a distal end 38 which defines the longitudinal length of the stent body. Each of the distal ends 38 of the elongated strut members 32 are attached and form the distal end 40 of the stent body. Likewise, the proximal ends 36 of each elongated strut member 32 are likewise attached to form the proximal end 42 of the stent. Alternatively, the proximal and distal ends of the elongated strut members could be attached to an expandable ring which would provide a more uniform edge for the ends of the stent. However, it is suitable for the ends of elongated strut members to be connected to each other to form the ends 40 and 42 of the stent.

Stent segment A is shown in greater detail in FIGS. 6-7. FIG. 6 is a plan view of stent segment A with the structure flattened out into two dimensions to facilitate explanation. FIG. 7 shows stent segment B is an expanded perspective view. In this particular embodiment of the present invention, the elongated strut members 32 have a serpentine or undulating pattern. This undulating shape can be, for example, alternating peaks 44 and valleys 46 as shown in FIGS. 1-3 and 6-7. The peaks 44 and valley 46, sometimes referred to as crests, curved portions, or irregular curved portions, can have many shapes including U-shapes, V-shapes, C-shapes, W-shapes or irregular radii-of-curvature-shapes, as disclosed in FIGS. 14 and 15 and discussed in greater detail below. Some of the peaks 44 on each elongate strut member are connected to a connecting link which is in turn connected to an adjacent elongate strut member. The elongate strut members and connecting links cooperatively form the tubular-shaped stent body. The number of peaks and valleys will depend upon the particular physical characteristics desired, along with the particular application to which the stent will be used.

The particular strut pattern shown in FIGS. 1-3 and 6-7 show the elongate strut members 32 having a plurality of alternating peaks 44 and valleys 46 wherein the peaks 44 of each elongate strut member are aligned with the peaks of the adjacent elongate strut members. Likewise, the valley portions 46 of each elongate strut member align with the valleys 46 of the adjacent elongate strut members. The term "in phase" in commonly used to describe this alignment of peaks and valleys of adjacent elongated strut members.

As can be seen in FIG. 6-7, the connecting links 34 connect adjacent elongate strut members such that an end 48 of the connecting link 34 is attached to the elongate strut members so that at least a portion of the connecting link 34 is positioned within one of the peaks 44 of that elongate strut member 32. The other end 50 of the connecting link 34 is attached, in turn, to a peak 44 of an adjacent elongated strut member. As can be seen in FIG. 6, the connecting link 34 does not connect peaks 44 of adjacent elongated strut members which are in phase with each, but rather, attaches peaks that are offset from each other. In this fashion, a larger connecting link 34 can be formed which allows the composite stent body to more readily expand to its expanded diameter as is shown in FIG. 7. Moreover, as can be seen best in FIG. 6, each connecting link 34 which attaches adjacent elongated strut members together are aligned end 48 to end 50 to create a helix pattern 52 which extends around the circumference of stent segment A. Dotted lines in FIG. 6 which shows the alignment of the connecting links which results in the formation of the helix pattern 52. It should be appreciated that only one side of the stent is shown in FIG. 6-7 and that the helix pattern repeats on the backside of the stent (not shown) to create a continuous helix along the entire length of the stent segment. It should be also appreciated that additional helix patterns of connecting links can be found on stent segment A as well. This additional helix extends between the helix pattern outlined by the dotted lines in FIGS. 6 and 7. For this reason, the stent segment may include one or more helical patterns which extend around the circumference of the stent to attain the stent characteristics associated with this pattern.

This particular stent pattern of stent segment A provides high fracture and fatigue resistant when the stent is subjected to torsional loading when placed in the patient's vasculature. This particular helix pattern of connecting links results in a large expanded radius allowing stress to be distributed over a greater area, thus resulting in less fatigue to the stent. This helical stent pattern provides excellent longitudinal flexibility while still providing good torsional flexibility once implanted in the patient. Stent segment A is particular suitable to be implanted arterial segments which are susceptible to torsional loading. For example, stent segment A would be particularly suitable for implanting in the mid proximal superficial femoral artery which is subject to compression loading. The continuous helical pattern of connecting links provides the needed structure which helps to prevent fracture and fatigue once stent segment A is implanted in this arterial segment.

Referring now to FIG. 8, stent segment B which forms part of the composite stent 10 of FIGS. 1-3 is shown in greater detail. In this particular stent pattern, a set of connecting links are placed along the stent body in a "stacked" configuration in which connecting links 34 are located laterally adjacent to each other in a plane that is substantially perpendicular to the stent longitudinal axis. Dotted lines define the stacked configuration S which results in the connecting links 34 being positioned directly laterally adjacent to each other to form a ring-like pattern that extends around the circumference of the stent body. Dotted lines also define a flex region F in which connecting links are missing to provide additional flexibility to stent segment B. As can be seen in FIGS. 6 and 7, several sets of connecting links are placed in the stacked configuration to create additional regions of high radial strength along the length of stent segment B. These alternating sets of stacked connecting links provide a stent pattern having increased radial strength but possessing a bit less flexibility than stent segment A. However, the stack configuration of connecting links provides an area of radial strength which is particular suitable to resisting bending fatigue and fracture resulting when stent segment B is implanted in an arterial segment that is prone to continuous bending or kinking. In this regard, this "stacked" configuration of connecting links provide superior radial force and strength which helps to prevent stent segment B from fatiguing and fracturing when subjected to the bending or kinking associated with an arterial segment such as the proximal superficial femoral artery or the distal femoral-popliteal segment The composite stent shown in FIGS. 1-3 is just one of the numerous combination of stent segments that can be achieved by the present invention. Accordingly, a composite stent including two or more stent segments can be manufactured to be implanted in a long arterial segment having different physiological deformations. It should be appreciated that although only two segments are shown connected to form the stent of FIGS. 1-3, more than two stent segments can be combined (as disclosed in other embodiments described below) to form a long stent body which matches particular stent segments to particular arterial segments. Also, the lengths and diameters (delivery diameter and expanded diameter) of the various segments can be varied, as needed, to create the appropriate length and radial size need for a given application.

Figure 9:
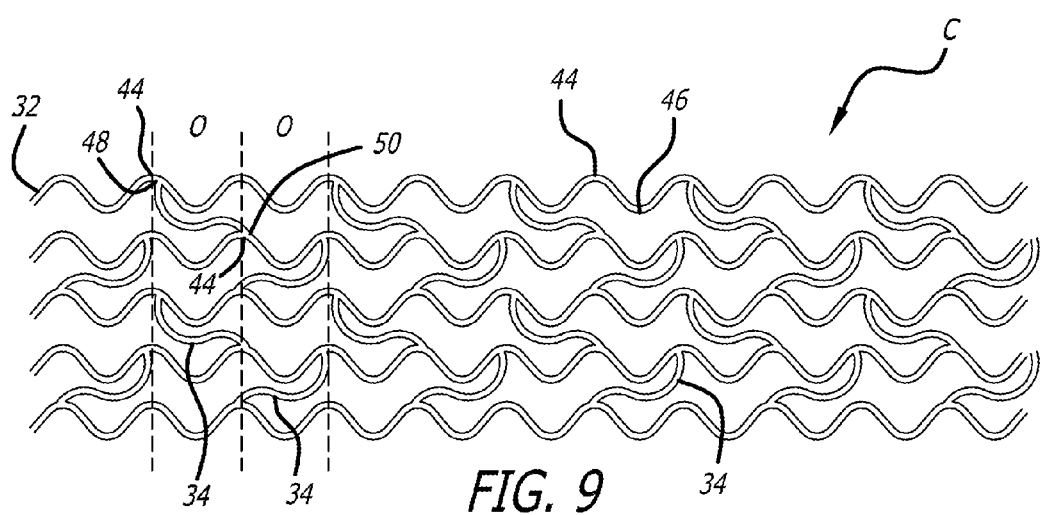
FIG. 9 is a plan view of another embodiment of a stent made in accordance with the present invention.

Referring now to FIG. 9, another embodiment of a stent segment C is shown. Stent segment C is a variation of the "stack" configuration of stent segment B as shown in FIG. 8. In this particular aspect of the invention, every other horizontal row of connecting links 34 in stent segment C is offset from another. As can be seen in FIG. 9, alternating elongate strut members 32 are connected by connecting links 34 such that the connecting links are positioned laterally adjacent to each other in a plane that is substantially perpendicular to the longitudinal stent axis. Again, dotted lines depict the alignment of alternating connecting links stacked adjacent to each other. This pattern differs from the "stacked" pattern of stent segment B in that there are alternating missing connecting links in the "stack." Accordingly, it is referred to a an "offset-stacked" configuration. As can be seen in FIG. 9, there are numerous offset-stacked sets of connecting links formed along the longitudinal length of the stent body. While this offset-stacked pattern does not attain the radial strength achieved with stent segment B, it nevertheless possesses sufficient radial strength to maintain the arterial wall in its expanded condition. However, due to this offset positioning of connecting links, flexibility along stent segment C is increased compared to stent segment B. As a result, radial strength and flexibility can be evenly blended throughout the length of stent segment C. Stent segment C is particularly useful in providing high fracture and fatigue resistance to axial loading, which is associated with the distal superficial femoral artery. For this reason, stent segment C would be particularly useful in a arterial segment which undergoes significant axial loading.

Figure 10:
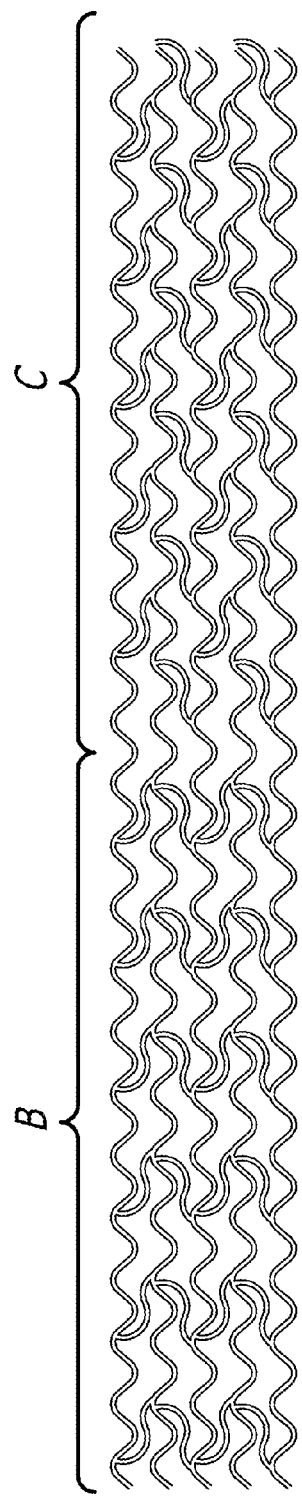
FIG. 10 is a plan view of another embodiment of a stent made in accordance with the present invention.

Referring now to FIGS. 10-13, composite stents made from various combinations of the stent segments A, B and C are disclosed. Referring initially to FIG. 10, a composite stent 50 made from stent segment B (FIG. 8) and segment C (FIG. 9) is shown. This composite stent 50 is particular suitable for implanting in a long arterial segment which is subject to bending or kinking and include a segment that is susceptible to axial loading. Accordingly, stent segment B would be implanted in the portion of the arterial segment which is susceptible to bending and kinking while stent segment C would be implanted in the portion of the arterial segment which is susceptible to axial deformation.

Figure 11:
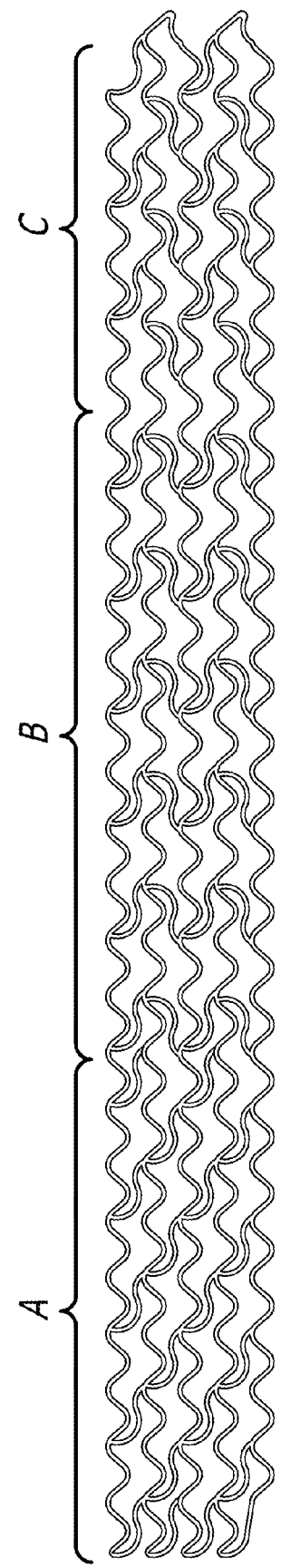
FIG. 11 is a plan view of another embodiment of a stent made in accordance with the present invention.
Figure 12:
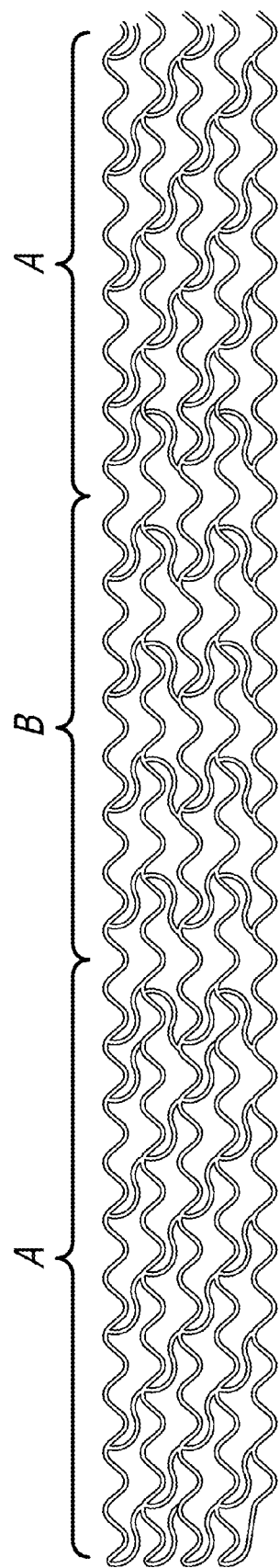
FIG. 12 is a plan view of another embodiment of a stent made in accordance with the present invention.
Figure 13:
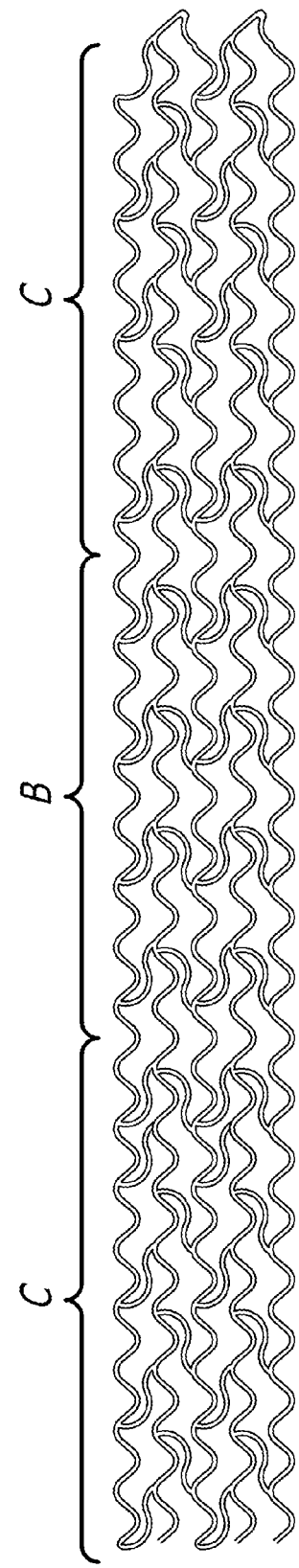
FIG. 13 is a plan view of another embodiment of a stent made in accordance with the present invention

FIG. 11 discloses a composite stent 60 created from the three stent segments A, B and C depicted in FIGS. 6-9. In this regard, stent segment A consisting of the helix pattern (FIGS. 6-7) is combined with the stacked configuration of segment B and the offset-stacked pattern of stent segment C. As a result, the composite stent 60 has three region of different stent performance characteristics that can be accordingly matched to particular arterial segments. FIG. 12 discloses a composite stent 70 made from stent segment A and stent segment B. The composite stent 80 depicted in FIG. 13 shows stent segment C located at ends of the composite stent 80 with stent segment B interposed between stent segments C. It should appreciated that there are numerous other combinations which can be achieved utilizing the various stent segments disclosed herein. Additional, more than three stent segments could be connected together to match the physiological deformations that may be associated with a long length of an arterial segment. Additionally, as stated above, a stent could be made from only one of the stent segments A, B and C described above for implantation in a particular arterial segment.

The composite stents disclosed herein are formed with elongate strut members which extend the entire length of the composite stent to define the longitudinal length of the composite stent. The stent patterns of the desired stent segment can be formed along the length of the elongate strut members to create the individual stent segment. Generally, as can be seen in FIGS. 9-13, the stent segments are spaced apart from each other by at least a pair of peaks and valleys which are free of any connection to a connecting link. It should be appreciated that a composite stent made in accordance with the present invention does not necessarily require the use of long elongate strut members to define the stent length. Rather, individual stent segments could be formed and connected together using one or more interconnecting members, such as connecting links.

Figure 14:
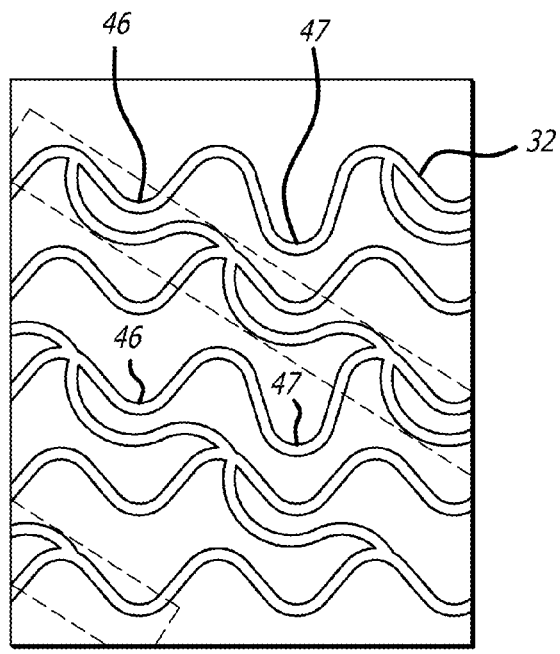
FIG. 14 is a plan view of a portion of a stent pattern showing the undulating portions of the elongate struts having varying amplitude.
Figure 15:
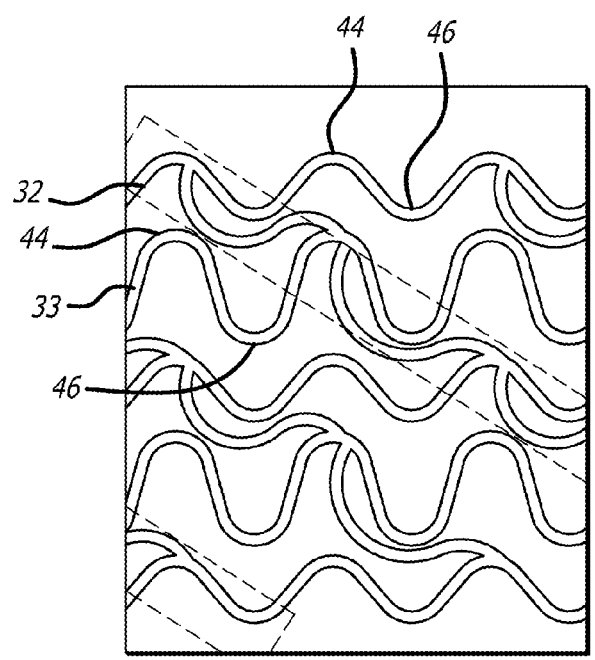
FIG. 15 is a plan view of a portion of a stent pattern showing the undulating portions of the elongate struts having different amplitudes.

Referring now to FIGS. 14-15, the size and shape of the undulating pattern of the elongated strut member 32 is shown having a non-uniform pattern. As can be seen in FIG. 14, some of the valley portions 47 are larger in amplitude than other valley portions 46 to create a structure that has more scaffolding ability. The longer valley portions 47 can be used to provide additional strut material in an area which may have some voids once expanded. This particular figure shows that the alternating peaks and valleys which form the elongate strut member does not have to be a uniform in amplitude (height or depth) but can be varied to have strut lengths which provide more scaffolding ability to the stent. Likewise, the height or amplitude of the peaks of the elongated strut members could be varied, as needed, to provide additional scaffolding to the composite stent.

Referring now to FIG. 15, the stent pattern shows the elongate members having different amplitudes to also provide additional scaffolding to the stent. As can be seen in FIG. 15, the amplitude of the undulating portion of several elongated strut members 33 are larger than adjacent elongated strut members 32 in order to provide more strut material to increase the scaffolding ability of the stent. The use of non-uniform shapes to create the peaks and valleys of the elongate strut members can allow for more even distribution of struts along the circumference of the stent body. It would be appreciated those skilled in the art that various forms of undulating patterns could be utilized in accordance with the present invention to create unique patterns to the elongated members in order to provide additional scaffolding to the stent.

For ease of illustration, the present invention has been depicted in a flattened plan view in most of the drawing figures herein. It should be noted, however, that all of the embodiments depicted herein are cylindrically-shaped stents that are generally formed from tubing by laser cutting as described below.

A suitable composition of Nitinol used in the manufacture of a self-expanding stent of the present invention is approximately 55% nickel and 44.5% titanium (by weight) with trace amounts of other elements making up about 0.5% of the composition. It should be appreciated that other compositions of Nitinol can be utilized, such as a nickel-titanium-platinum alloy, to obtain the same features of a self-expanding stent made in accordance with the present invention.

The stent of the present invention can be laser cut from a tube of nickel titanium (Nitinol). All of the stent diameters can be cut with the same stent pattern, and the stent is expanded and heat treated to be stable at the desired final diameter. The heat treatment also controls the transformation temperature of the Nitinol such that the stent is superelastic at body temperature. The transformation temperature is at or below body temperature so that the stent will be superelastic at body temperature. The stent can be electro-polished to obtain a smooth finish with a thin layer of titanium oxide placed on the surface. The stent is usually implanted into the target vessel which is smaller than the stent diameter so that the stent applies a force to the vessel wall to keep it open.

The stent tubing of a stent made in accordance with the present invention may be made of suitable biocompatible material besides nickel-titanium (NiTi) alloys. It should be appreciated the stent patterns of the present invention also can be used with balloon expandable stents as well. In this case, the stent would be formed using known techniques for manufacturing balloon expandable stents as well. The tubing may be made, for example, a suitable biocompatible material such as stainless steel. The stainless steel tube may be alloy-type: 316L SS, Special Chemistry per ASTM F138-92 or ASTM F139-92 grade 2. The stent of the present invention also can be made from a metallic material or an alloy such as, but not limited to, cobalt chromium alloy (ELGILOY), MP35N, MP20N, ELASTINITE, tantalum, platinum-iridium alloy, gold, magnesium, or combinations thereof. MP35N and MP20N are trade names for alloys of cobalt, nickel, chromium and molybdenum available from Standard Press Steel Co., Jenkintown, Pa. MP35N consists of 35% nickel, 20% chromium, and 120% molybdenum. MP20N consists of 50% cobalt, 20% nickel, 20% chromium, and 20% molybdenum. Stents also can be made from bioabsorbable or biostable polymers.

One method of making the stent, however, is to cut a thin-walled tubular member, such as Nitinol tubing, and remove portions of the tubing in the desired pattern for the stent, leaving relatively untouched the portions of the metallic tubing which are to form the stent. The tubing can be cut in the desired pattern by means of a machine-controlled laser.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished stent. Further details on how the tubing can be cut by a laser are found in U.S. Pat. No. 5,759,192 (Saunders), U.S. Pat. No. 5,780,807 (Saunders) and U.S. Pat. No. 6,131,266 (Saunders), which are incorporated herein in their entirety.

The process of cutting a pattern for the stent into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

After the stent has been cut by the laser, electrical chemical polishing, using various techniques known in the art, should be employed in order to create the desired final polished finish for the stent. The electropolishing will also be able to take off protruding edges and rough surfaces which were created during the laser cutting procedure.

Any of the stents disclosed herein can be coated with a drug for treating the vascular system. The drug, therapeutic substance or active agent, terms which are used interchangeably, in the coating can inhibit the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect for a diseased condition. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich, Inc., Milwaukee, Wis.; or COSMEGEN available from Merck & Co., Inc., Whitehorse Station, N.J.). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack, N.J.), and mitomycin (e.g., Mutamycin® from Bristol-Myers Squibb Co.). Examples of such antiplatelets, anticoagulants, antifibrin, and antithrombins include sodium heparin, low molecular weight heparins, heparinoids, hirudin, argatroban, forskolin, vapiprost, pro-arg-chloromethylketone (synthetic antithrombin), dipyridamole, flycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co.), cilazapril or lisinopril (e.g., Prinvil® and Prinzide® from Merck & Co., Inc.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and it derivatives and analogs, and dexamethasone.

Coating 20 can be made from any suitable biocompatible polymer, examples of which include ethylene vinyl alcohol copolymer (commonly known by the generic name EVOH or by the trade name EVAL); poly(hydroxyvalerate); poly(L-lactic acid); polycaprolactone; poly(lactide-co-gly-colide); poly(hydroxybutyrate); poly(hydroxybutyrate-co-valerate); polydioxanone; polyorthoester; polyanhydride; poly(glycolic acid); poly(D,L-lactic acid); poly(flycolic acid-co-trimethylene carbonate); polyphosphoester; poly-phosphoester urethane; poly(aminoacids); cyanoacrylates; poly(trimethylene carbonate); poly(iminocarbonate); copoly(ether-esters) (e.g., PEO/PLA); polyalkylene oxalates; poly-phosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones, polyvinyl aromatics, such as polystyrene; polyvinyl esters, such as polyvinyl acetate; copolymers of vinyl monomers with each other and olefins, such as ethylenemethyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose. Coating 20 can also be silicon foam, neoprene, santoprene, or closed cell foam.

Although the present invention has been described in terms of certain preferred embodiments, other embodiments that are apparent to those of ordinary skill in the art are also within the scope of the invention. Accordingly, the scope of the invention is intended to be defined only by reference to the appended claims. While the dimensions, types of materials and coatings described herein are intended to define the parameters of the invention, they are by no means limiting and are exemplary embodiments.

What is claimed is:

1. A stent, comprising:
a plurality of elongate strut members spaced apart, each elongate strut member extending lengthwise to define a longitudinal axis, each elongate strut member having a plurality of alternating peaks and valleys, the peaks and valleys of each elongate strut member being in phase with the peaks and valleys of adjacent elongate members; and
a first set of connecting links connecting elongate strut members together to form a tubular stent body, each of the connecting links of the first set attaching a peak of one elongated strut member to a peak of an adjacent elongated strut member which is offset from that peak, the first set of connecting links being disposed laterally adjacent to each other about the tubular stent body to form a first stacked region on the tubular stent body;
a second set of connecting links connecting elongate strut members together to form the tubular stent body, each of the connecting links of the second set attaching a peak of one elongate strut member to a peak of an adjacent elongated strut member which is offset from that peak, the second set of connecting links being disposed laterally adjacent to each other about the tubular stent body to form a second stacked region on the tubular stent body; and
a flex region formed between the first and second stacked regions.

2. The stent of claim 1, wherein each of the connecting links of the first set and the second set attaches an elongate strut member to an adjacent elongate strut member so that at least a portion of the connecting link is positioned within the peak as it attaches that peak to a peak of an adjacent elongate strut member.

3. The stent of claim 1, wherein the flex region includes a valley on each of the elongate strut members.

4. A stent, comprising:
a plurality of elongate strut members spaced apart, each elongate strut member extending lengthwise to define a longitudinal axis, each elongate strut member having a plurality of alternating peaks and valleys, the peaks and valleys of each elongate strut member being in phase with the peaks and valleys of adjacent elongate members; and
connecting links connecting adjacent elongate strut members together to cooperatively form a tubular stent body, some of the connecting links being arranged along the tubular body to form a first offset-stacked configuration in which the connecting links connect the peak of one elongated strut member to a peak of an adjacent elongated strut member, wherein alternating elongate strut members are connected by the connecting links, the connecting links being disposed laterally adjacent to each other about the tubular stent body; and
some of the connecting links arranged along the tubular body to form a second offset-stacked configuration in which the connecting links connect the peak of one elongated strut member to a peak of an adjacent elongated strut member, wherein alternating elongate strut members are connected by the connecting links, the connecting links being disposed laterally adjacent to each other about the tubular stent body.

5. The stent of claim 4, wherein each of the connecting links attaches elongate strut members together so that at least a portion of the connecting link is positioned within the peak as it attaches that peak to a peak of an adjacent elongate strut member.

6. The stent of claim 4, wherein the first offset-stacked configuration is adjacent to the second offset-stacked configuration.

* * * * *